(12) United States Patent
Mickles et al.

(10) Patent No.: US 11,755,991 B2
(45) Date of Patent: *Sep. 12, 2023

(54) SYSTEM AND METHOD FOR BLOOD COMPONENT SUPPLY CHAIN MANAGEMENT

(71) Applicant: Fenwal, Inc., Lake Zurich, IL (US)

(72) Inventors: Kathleen Mickles, Woodridge, IL (US); Dale H. Meixelsperger, Gurnee, IL (US); Brent Paul, Libertyville, IL (US); Todd Lewis, Bettendorf, IA (US); Christopher Trussell, Springfield, MO (US); Adam Bryan, Chicago, IL (US); Dean Gregory, Northbrook, IL (US); William H. Cork, Mettawa, IL (US)

(73) Assignee: Fenwal, Inc., Lake Zurich, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/129,696

(22) Filed: Dec. 21, 2020

(65) Prior Publication Data

US 2021/0110337 A1    Apr. 15, 2021

Related U.S. Application Data

(62) Division of application No. 14/142,575, filed on Dec. 27, 2013, now Pat. No. 10,872,307.

(51) Int. Cl.
*G06Q 10/087* (2023.01)
*G16H 40/20* (2018.01)

(52) U.S. Cl.
CPC ........... *G06Q 10/087* (2013.01); *G16H 40/20* (2018.01)

(58) Field of Classification Search
None
See application file for complete search history.

(56) References Cited

U.S. PATENT DOCUMENTS

| 6,786,405 B2 * | 9/2004 | Wiedenhoefer | G16H 40/60 235/462.46 |
| 6,983,884 B2 * | 1/2006 | Auchinleck | G16H 40/20 435/372 |

(Continued)

FOREIGN PATENT DOCUMENTS

| WO | WO-2010/088466 A1 | 8/2010 | |
| WO | WO-2013/090531 A1 | 6/2013 | |
| WO | WO-2013090531 A1 * | 6/2013 | ....... G01N 35/00663 |

OTHER PUBLICATIONS

Frankfurter et al, Management control of blood through a short-term supply-demand forecast system, Management Science, 21 No. 4, pp. 444-452, Dec. 1974 http://www.jstor.org/stable/pdf/2629616.pdf (Year: 1974).*

(Continued)

*Primary Examiner* — Octavian Rotaru
(74) *Attorney, Agent, or Firm* — Foley & Lardner LLP

(57) ABSTRACT

Systems and methods for managing inventories of blood components are disclosed. Such systems and methods are configured to improve the predictability, efficiency, and/or automation of blood component supply chains. Tools are provided for tracking blood component inventories, forecasting blood component demand, and coordinating donations to meet current and anticipated demand. Some embodiments of the systems and methods identify when blood component units at a health care facility are beginning to run low or are approaching expiration, before the need for additional units becomes critical. Some embodiments of the systems and methods coordinate new donations and modify existing scheduled donations to meet real-time and forecasted demand for blood components.

20 Claims, 7 Drawing Sheets

(56) References Cited

U.S. PATENT DOCUMENTS

| | | | | |
|---|---|---|---|---|
| 7,237,713 B2* | 7/2007 | White | G06Q 10/087 | 340/5.91 |
| 7,720,708 B1* | 5/2010 | Elkins, II | G06Q 30/0207 | 705/14.1 |
| 7,769,603 B2* | 8/2010 | Jung | G16H 10/60 | 705/2 |
| 8,005,622 B2* | 8/2011 | Hauck | G16H 20/17 | 707/769 |
| 8,032,306 B2* | 10/2011 | Hauck | A61M 1/02 | 707/769 |
| 8,156,158 B2* | 4/2012 | Rolls | G16H 10/60 | 707/809 |
| 8,204,694 B2* | 6/2012 | Hauck | G16H 40/67 | 707/769 |
| 8,229,675 B2* | 7/2012 | Csore | A61B 5/0002 | 702/19 |
| 8,318,499 B2* | 11/2012 | Fritchie | G01N 35/00584 | 422/50 |
| 8,430,922 B2* | 4/2013 | Jung | G16H 20/10 | 623/1.13 |
| 8,475,517 B2* | 7/2013 | Jung | A61B 1/3137 | 705/2 |
| 8,484,049 B2* | 7/2013 | Mullenger | G16H 10/40 | 705/3 |
| 8,550,344 B2* | 10/2013 | Jung | G06Q 10/06 | 705/28 |
| 8,551,155 B2* | 10/2013 | Jung | A61B 1/00082 | 705/2 |
| 8,577,693 B2* | 11/2013 | Jung | G16H 40/20 | 705/2 |
| 8,676,600 B2* | 3/2014 | Case | G16H 40/63 | 705/2 |
| 8,721,706 B2* | 5/2014 | Jung | G16H 20/40 | 705/2 |
| 8,782,543 B2* | 7/2014 | Foley | G16H 40/63 | 715/764 |
| 9,697,337 B2* | 7/2017 | Goodnow, II | G16H 10/40 | |
| 11,038,848 B2* | 6/2021 | Armitage | H04L 63/0421 | |
| 11,228,567 B2* | 1/2022 | Armitage | G16H 40/20 | |
| 2001/0034614 A1* | 10/2001 | Fletcher-Haynes | A61M 1/3693 | 705/2 |
| 2002/0013523 A1* | 1/2002 | Csore | G16H 10/40 | 705/2 |
| 2003/0004751 A1* | 1/2003 | Ng | G16H 15/00 | 705/2 |
| 2003/0018289 A1* | 1/2003 | Ng | G16H 10/20 | 210/782 |
| 2003/0040835 A1* | 2/2003 | Ng | A61B 5/150786 | 700/214 |
| 2003/0040938 A1* | 2/2003 | Ng | G16H 15/00 | 705/2 |
| 2003/0069480 A1* | 4/2003 | Ng | A61B 5/150786 | 600/300 |
| 2003/0078805 A1* | 4/2003 | Ng | A61B 5/15003 | 705/2 |
| 2003/0078808 A1* | 4/2003 | Ng | A61B 5/150786 | 705/3 |
| 2003/0154108 A1* | 8/2003 | Fletcher-Haynes | G16H 10/40 | 705/3 |
| 2003/0158673 A1* | 8/2003 | Grosse | G16B 50/00 | 702/19 |
| 2004/0039607 A1* | 2/2004 | Savitz | G16H 10/40 | 705/3 |
| 2004/0044326 A1* | 3/2004 | Kranz | A61B 90/96 | 604/408 |
| 2004/0117196 A1* | 6/2004 | Brockman | G06Q 40/12 | 705/332 |
| 2005/0071245 A1* | 3/2005 | Norins, Jr. | G06Q 10/02 | 705/14.35 |
| 2005/0131738 A1* | 6/2005 | Morris | G16H 40/63 | 705/2 |
| 2005/0184153 A1* | 8/2005 | Auchinleck | G16H 40/20 | 235/385 |
| 2005/0209883 A1* | 9/2005 | Fletcher-Haynes | A61M 1/0286 | 705/2 |
| 2006/0008859 A1* | 1/2006 | Seul | G16H 10/60 | 435/7.25 |
| 2006/0136137 A1* | 6/2006 | Hauck | G16H 20/17 | 702/19 |
| 2006/0178909 A1* | 8/2006 | Hauck | G16H 40/20 | 705/28 |
| 2007/0106754 A1* | 5/2007 | Moore | G16H 40/20 | 707/E17.116 |
| 2007/0219826 A1* | 9/2007 | Brodsky | G16H 10/20 | 705/2 |
| 2007/0293756 A1* | 12/2007 | Jung | G06Q 10/06 | 600/427 |
| 2007/0293966 A1* | 12/2007 | Jung | G06Q 10/06 | 600/36 |
| 2007/0294150 A1* | 12/2007 | Jung | G06Q 10/06 | 705/28 |
| 2007/0294151 A1* | 12/2007 | Jung | G06Q 10/087 | 705/28 |
| 2007/0294152 A1* | 12/2007 | Jung | G06Q 10/087 | 705/28 |
| 2007/0294210 A1* | 12/2007 | Jung | A61B 5/411 | |
| 2008/0027751 A1* | 1/2008 | Pappalardo | G16H 20/13 | 600/300 |
| 2008/0033744 A1* | 2/2008 | Jones | G06Q 30/0279 | 705/329 |
| 2008/0040151 A1* | 2/2008 | Moore | G16H 40/67 | 705/2 |
| 2008/0077433 A1* | 3/2008 | Kasprisin | G16H 40/20 | 600/300 |
| 2008/0126127 A1* | 5/2008 | Bobroff | G16H 20/00 | 705/2 |
| 2008/0208750 A1* | 8/2008 | Chen | G06Q 10/0833 | 340/572.1 |
| 2008/0262948 A1* | 10/2008 | Grady | G06Q 30/04 | 705/28 |
| 2009/0076856 A1* | 3/2009 | Darby | G09B 23/28 | 705/2 |
| 2009/0089099 A1* | 4/2009 | Kranz | G16H 10/40 | 705/3 |
| 2009/0187424 A1* | 7/2009 | Grabowski | G16H 40/63 | 705/2 |
| 2009/0313042 A1* | 12/2009 | Zhang | G06Q 30/02 | 705/2 |
| 2009/0313071 A1* | 12/2009 | Hehenberger | G16H 40/40 | 705/28 |
| 2010/0049542 A1* | 2/2010 | Benjamin | G06Q 10/0637 | 705/28 |
| 2010/0088466 A1* | 4/2010 | Nakanishi | G06F 3/0613 | 711/E12.008 |
| 2010/0106516 A1* | 4/2010 | Hannon | G06Q 10/087 | 705/2 |
| 2011/0202170 A1* | 8/2011 | Dawes | G16H 40/67 | 700/214 |
| 2011/0213625 A1* | 9/2011 | Joao | G16H 20/40 | 705/2 |
| 2011/0270708 A1* | 11/2011 | Walden | G06Q 10/087 | 705/28 |
| 2012/0010062 A1* | 1/2012 | Fletcher | A61M 1/3693 | 494/60 |
| 2012/0038651 A1* | 2/2012 | Case | G06Q 10/087 | 345/440 |
| 2012/0041776 A1* | 2/2012 | Minato | G16H 40/20 | 705/2 |
| 2012/0041777 A1* | 2/2012 | Case | G06Q 10/1093 | 705/28 |
| 2012/0109677 A1* | 5/2012 | Hillyer | G16H 10/40 | 435/7.25 |
| 2012/0138533 A1* | 6/2012 | Curtis | A61M 1/16 | 210/85 |
| 2012/0203567 A1* | 8/2012 | Seul | G06Q 10/06315 | 705/2 |

(56) References Cited

U.S. PATENT DOCUMENTS

| | | | | |
|---|---|---|---|---|
| 2012/0271740 | A1* | 10/2012 | Connors | G06Q 10/087 |
| | | | | 705/28 |
| 2013/0159135 | A1* | 6/2013 | Jones | G06Q 10/08 |
| | | | | 705/26.8 |
| 2013/0274245 | A1* | 10/2013 | Blumenstein | A61P 9/02 |
| | | | | 514/211.07 |
| 2014/0128838 | A1* | 5/2014 | Satish | G06T 7/0012 |
| | | | | 604/503 |
| 2014/0136233 | A1* | 5/2014 | Atkinson | G16H 15/00 |
| | | | | 705/3 |
| 2014/0195254 | A1* | 7/2014 | McElroy | G16H 40/20 |
| | | | | 705/2 |
| 2014/0278499 | A1* | 9/2014 | Bowman | G06Q 30/0601 |
| | | | | 705/2 |
| 2016/0005139 | A1* | 1/2016 | Hannon | G06Q 10/087 |
| | | | | 705/2 |

OTHER PUBLICATIONS

European Search Report on EP 20186748.8 dated Dec. 10, 2020.
Frankfurter, et al., "Management control of blood through a short-term supply-demand forecast system," Management Science 21(4), pp. 444-452 (1974).
International Search Report and Written Opinion on PCT Application No. PCT/US2014/070380, dated Sep. 21, 2015, 23 pages.
Kebo et al., "The Potential of RFID Technology in Blood Center Processes", Studies in health technology and informatics, Jan. 1, 2010, pp. 71-77.
PCT International Preliminary Report on Patentability for PCT/US2014/070380 dated Jul. 7, 2016. 18 pages.

\* cited by examiner

SYSTEM AND METHOD FOR BLOOD COMPONENT SUPPLY CHAIN MANAGEMENT

CROSS-REFERENCE TO RELATED APPLICATION

This application is a divisional application of and claims the benefit of U.S. patent application Ser. No. 14/142,575, filed Dec. 27, 2013, which is incorporated herein by reference in its entirety.

FIELD OF THE INVENTION

The present technology relates to supply chain management, and is particularly directed to the management of blood and blood component inventories.

BACKGROUND

Blood components, such as red blood cells, platelets, and plasma, are frequently used in transfusion facility settings to treat injury and disease. For example, red blood cell transfusions are often performed for patients suffering from anemia, platelet transfusions are frequently performed to limit bleeding and hemorrhaging in patients with excessive bleeding, bleeding disorders, or hematologic malignancies, and plasma, platelets, red blood cells, and/or whole blood may be transfused during surgical procedures to replace blood or blood components that have been lost. The amount of blood components needed for any particular surgery or treatment is difficult to predict, varying, for example, by procedure, patient characteristics, and encountered complications. Blood components are often needed under emergency conditions, and health care facilities sometimes do not have a reliable method to monitor their blood component usage. As a result, the facility may find that they have excess blood components or not enough of the blood component products needed to meet their transfusion demand.

When a health care facility is in need of additional blood components, the health care facility orders the products from a blood center. Blood centers coordinate with individual donors and blood donation drive managers to obtain needed blood components. It can be extremely difficult for blood centers to predict when health care facilities will need blood components and which blood components they will need. It can also be extremely difficult to coordinate donations to match the current needs.

If blood centers keep too few reserves on hand, health care facilities face delays in obtaining new inventory, which can be life-threatening for patients, and blood centers risk losing customers (e.g., hospitals) that look to other blood centers to find the inventories they need. Moreover, shortages in blood components can raise the market price of such products significantly, leading to higher medical costs. Conversely, if blood centers keep too many reserves on hand, the perishable inventory will expire before it is ever used, generating unnecessary waste in the system. Thus, there is a need for improved coordination within the blood components supply chain.

SUMMARY

One aspect of the disclosure is directed to a method of tracking current blood component inventory at the blood center and health care facility. In various disclosed embodiments, the method includes maintaining an inventory log documenting the blood component inventory at the facility. The inventory log includes a count of blood component units currently in the inventory for each of a plurality of blood components. The log also includes identification data, such as a unique identifier, a component type, a blood type, and an expiration date, for each blood component unit. Another method for tracking current inventory includes receiving a signal indicating stocking or removal of a blood component from the inventory, wherein the data transmitted in the signal includes the unique identifier of the added or removed blood component unit. The method further includes adding or deducting the respective blood component unit from the inventory log. When a blood component has been removed from the inventory, the method also includes assessing the inventory log to determine if the count of blood component units for any of the plurality of blood components has fallen below an alert threshold. If the count of blood component units for any of the blood components has fallen below the alert threshold, the method also includes notifying the health care facility or a blood center of the low supply.

Another aspect of the disclosure is directed to a system for tracking current blood component inventory in a blood component supply chain. In some embodiments, the system includes a non-transitory computer readable medium, such as a computer readable medium that stores instructions, which when executed, cause a computer to perform the method described above. The system also includes a processor configured to execute instructions stored on the computer readable medium, a wireless receiver configured to receive data transmitted from an RFID reader-coupled computer, and a wireless transmitter configured to transmit data to a user workstation.

Additional embodiments of a system for tracking current blood component inventory in a blood component supply chain are described herein. For example, in one disclosed embodiment, the system includes: an RFID reader configured to detect and interrogate an RFID chip located on a blood component; an RFID reader-coupled computer located onboard the RFID reader or communicatively coupled to the RFID reader, the RFID reader-coupled computer including a processor, memory, an input for receiving RFID reader signals, and a wireless transmitter; a user workstation that includes a user interface with an input and output device, a processor, memory, and a wireless receiver; and an inventory management computer. In various embodiments, the inventory management computer includes a wireless receiver and transmitter, a processor, and a memory storing instructions, which when executed by the processor, cause the inventory management computer to implement a method for tracking current blood component inventory. In some embodiments, the implemented method provided for in the instructions is one of the methods for tracking current inventory described above or elsewhere herein. In some embodiments, the inventory management computer is a server wirelessly connected to the RFID reader-coupled computer and the user workstation via a communication network.

An additional aspect of the disclosure is directed to a method of generating new blood component inventory to address anticipated or current demand in a blood component supply chain. In some embodiments, the method includes: receiving input data identifying a present donor; accessing stored scheduling data to identify a scheduled appointment for the present donor, the scheduling data including an identification of a scheduled blood component to be collected from the present donor; accessing a user profile of the present donor; and determining, at least in part from the scheduling data and the user profile, whether the scheduled appointment is optimized. In some embodiments, the scheduled appointment is optimized if: the scheduled blood component is a needed blood component for which there is current or anticipated demand, and a donation potential of the present donor is maximized. In some embodiments, the method further includes recommending a modification to the scheduled appointment or scheduled blood component to be collected at that time if the original appointment or blood component to be collected is not optimized.

A further aspect of the disclosure is directed to a system for generating new blood component inventory to address anticipated or current demand in a blood component supply chain. Various embodiments of the system include a user workstation and an inventory management computer. In various embodiments of the system, the user workstation includes a processor, memory, an input configured to receive identification data uniquely identifying a present donor, and a wireless transmitter and receiver. The inventory management computer of various embodiments includes a wireless receiver and transmitter, a processor, and a memory storing instructions. When such instructions are executed by the processor, the inventory management computer implements a method for generating new blood component inventory to address anticipated or current demand, such as any such methods described herein. For example, in some embodiments, the instructions, when executed, cause the inventory management computer to: receive input data from the user workstation identifying the present donor; access stored scheduling data to identify a scheduled appointment for the present donor where the scheduling data includes an identification of a scheduled blood component to be collected from the present donor; access a user profile of the present donor; and determine, at least in part from the scheduling data and the user profile, whether the scheduled appointment is optimized. In some embodiments, the scheduled appointment is not optimized if the present donor is not scheduled to donate a full capacity of a donor's potential. The donor's potential is defined as a safe maximum number of blood components capable of being donated based on donor characteristics, device criteria and inventory level. In some embodiments, the scheduled appointment is not optimized if the scheduled blood component is not a needed blood component for which there is current or anticipated demand. In some embodiments, the blood component supply chain management computer also recommends a modification to the scheduled appointment if it is not optimized and transmits the recommendation for display at the user workstation.

Yet another aspect of the disclosure is directed to an additional method for generating new blood component inventory to address anticipated or current demand in a blood component supply chain. In some embodiments, the method includes: identifying anticipated or current demand for a needed blood component; accessing a scheduling log comprising a plurality of appointments for scheduled blood component collections; comparing the plurality of scheduled blood component collections to the needed blood component to identify at least one optimal target scheduled donor whose scheduled blood component collection is not for the needed or highest priority blood component; accessing a user profile of the target scheduled donor to determine if the target scheduled donor is eligible to donate the needed blood component; and if the target scheduled donor is eligible, recommending a modification to the scheduled blood component collection. In various embodiments, scheduled blood component collections are thus optimized to best match need.

A further aspect of the disclosure is directed to a non-transitory computer readable medium storing instructions, which when implemented, cause a processor to perform a method for generating new optimal blood component inventory to address anticipated or current demand in the blood component supply chain. In some embodiments, the performed method for generating new inventory is one of the methods described above or elsewhere herein.

Another aspect of the disclosure is directed to a system for generating new blood component inventory to address anticipated or current demand in a blood component supply chain. In some embodiments, the system includes a non-transitory computer readable medium, such as the computer readable medium described above. The system also includes a processor configured to execute instructions stored on the non-transitory computer readable medium, a wireless receiver configured to receive identification data from a user workstation, which uniquely identifies a present donor, and a wireless transmitter configured to transmit data to the user workstation.

BRIEF DESCRIPTION OF THE DRAWINGS

Exemplary embodiments are described below with reference to the accompanying drawings, wherein like numerals denote like elements, and.

DETAILED DESCRIPTION

Figure 1:
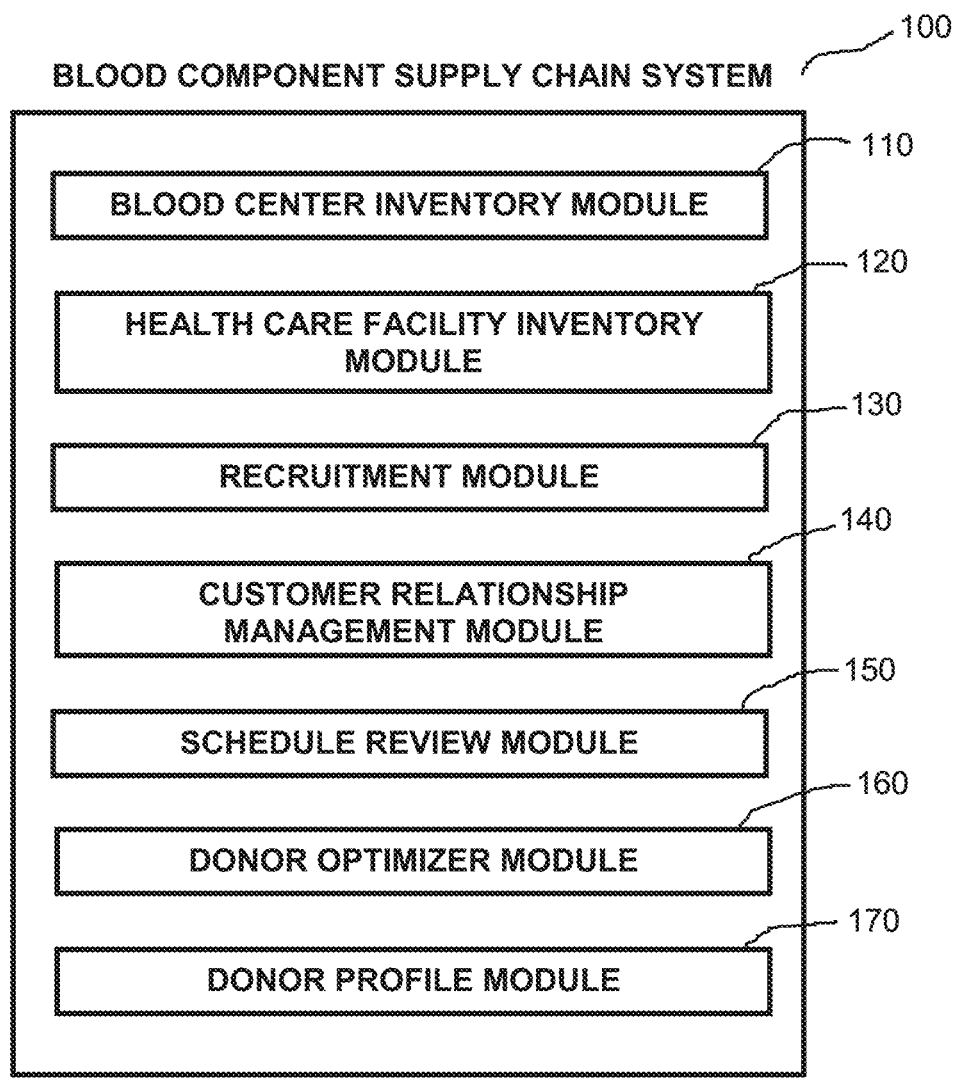
FIG. 1 is a general schematic block diagram depicting various functional modules of a blood component supply chain management system in accordance with one exemplary embodiment.

In the following detailed description, reference is made to the accompanying drawings, which form part of the present disclosure. The embodiments described in the drawings and description are intended to be exemplary and not limiting. As used herein, the term "exemplary" means "serving as an example or illustration" and should not necessarily be construed as preferred or advantageous over other embodiments. Other embodiments may be utilized and modifications may be made without departing from the spirit or the scope of the subject matter presented herein. Aspects of the disclosure, as described and illustrated herein, can be arranged, combined, and designed in a variety of different configurations, all of which are explicitly contemplated and form part of this disclosure.

Unless otherwise defined, each technical or scientific term used herein has the same meaning as commonly understood by one of ordinary skill in the art to which this disclosure belongs. In accordance with the claims that follow and the disclosure provided herein, the following terms are defined with the following meanings, unless explicitly stated otherwise.

The term "about" or "approximately," when used before a numerical designation or range indicates approximations which may vary by (+) or (−) 5%, 1%, or 0.1%.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a device or method consisting essentially of the elements as defined herein would not exclude other materials or steps that do not materially affect the basic and novel characteristic(s) of the claimed invention. "Consisting of" shall mean that the devices, systems, and methods include the recited elements and exclude anything more than a trivial or inconsequential element or step. Embodiments defined by each of these transitional terms are within the scope of this disclosure.

As used herein in the specification and claims, the singular form "a," "an" or "the" include both singular and plural references unless the context clearly dictates otherwise. For example, and without limitation, "a blood component" includes one or more blood components, and "a donor" may refer to one or a plurality of donors. At times, the claims and disclosure may include terms such as "a plurality," "one or more," or "at least one;" however, the absence of such terms is not intended to mean, and should not be interpreted to mean, that a plurality is not conceived.

As used herein, "health care facility" shall refer to any hospital, urgent care facility, health care clinic, medical tent, or other location where blood component transfusions and/or other health care treatment is rendered.

As used herein, "blood component" or "blood components" shall refer to packaged blood and/or packaged blood components such as, for example, platelets, plasma, or red blood cells (RBCs).

Embodiments disclosed herein generally relate to improved systems and methods for managing inventories of blood components. Specifically, this disclosure relates to systems and methods for improving the predictability, efficiency, and/or automation of blood component supply chains. Various systems and methods provide tools for: tracking blood component inventories, forecasting blood component demand, and coordinating donations to better match new supply to current demand.

As mentioned above, hospitals and other health care facilities consume blood components regularly and have a frequent, reoccurring need for blood components. Systems have been developed to help manage portions of the blood component supply chain, with some systems purporting to be total inventory management systems; however, existing systems have substantial shortcomings.

Some existing systems allow for inventory tracking from donation to a blood center. Such systems allow blood centers to see what blood components they have in stock, and potentially, the expiration date of such products. However, with such systems, inventory tracking generally stops at the blood center. These systems fail to provide blood centers with meaningful information about the status of blood components once they leave the blood center. Thus, with these existing systems, it is impossible to track inventory and usage within a health care facility. These systems provide blood centers little benefit when they are trying to predict future demand.

Moreover, some systems on the market include customer relationship management tools that enable blood centers to: store contact information and other basic information about past donors, reach out to past donors when additional blood components are needed, and schedule donation times for donors. However, with various existing systems, donor recruitment is independent of demand. In other systems, donor recruitment is triggered when a health care facility places an order. This can be problematic, because the process for recruiting donors and planning donation drives and/or individual donations can often take days, weeks, or months. In addition, the type of donation to occur is typically determined at the time of scheduling, which again, may be days or weeks in advance of the donation. Thus, these current systems do not enable blood centers to quickly respond to changes in demand.

A need exists for systems and methods for tracking blood component inventory through every stage of the supply chain. A need exists for systems and methods that can identify when blood component supplies at a health care facility are beginning to run low or are approaching expiration, far before the need for additional supplies becomes critical. A need also exists for systems and methods that coordinate new donations and optimize existing scheduled donations to meet current, real-time demands and anticipated demands for blood components. Certain embodiments disclosed herein may fulfill one or more of these needs.

System Functionality

Various embodiments provided herein include systems for tracking current blood component inventory in a blood component supply chain and systems for generating new blood component inventory to address anticipated or current demand in the supply chain. Some embodiments of the systems are configured to track current blood component inventory, identify anticipated and/or current demand, or generate new inventory to address such demand. Some embodiments of the systems provide for continued review of existing blood component inventory levels, optimal inventory levels, and device utilization, as compared to an existing collection schedule, allowing for optimal revisions to the collection schedule, and thus allowing for the ability to balance blood component collections and blood component inventory within the system. Each of the above recited systems can be referred to generally as a blood component supply chain management system. Various functions performed by some or all of the blood component supply chain management systems contemplated herein are shown in FIG. 1 and described in detail below. Various embodiments of blood component supply chain management systems disclosed herein are computerized and some or all of the functions performed by the system are performed by one or more computers. Specific components that may form the system are described in more detail below following the discussion of the system's functionality.

As shown in FIG. 1, some embodiments of a blood component supply chain management system 100 include a Blood Center Inventory Module 110. Such a module tracks the inventory of a blood center allowing the blood center to know exactly what supply of blood components it has in its reserves. In some embodiments, a log of the blood center's inventory is stored in a computer database. Blood component units added to the inventory are added to the inventory log and blood component units removed from the inventory are removed from the inventory log. The inventory log includes details about the blood component units stored in the blood center's inventory. For example, in some embodiments, the inventory log at least includes a unique identifier, the component type, the blood type, and the expiration date for each blood component unit. As further example, an entry for a particular blood component bag may list: a number or other code uniquely identifying the bag; an indication of whether the bag contains whole blood, plasma, platelets, RBC, etc. (i.e., the component type); an indication of whether the bag contains components from A, B, AB, or O blood (i.e., the blood type); and the date at which the blood component is no longer safe for transfusion into humans (i.e., the expiration date). Additional blood component characteristics, including but not limited to, the date the blood component was donated, may also be included. In some embodiments, some or all such information is contained within, embedded within, or encoded within the unique blood component identifier. In some embodiments, some or all such information is contained within, embedded within, or encoded within a bar code, RFID code, or other scannable or graphical representation of data.

In some embodiments, a bag's entry into the blood center's inventory and exit from said inventory is tracked electronically and its status is automatically updated in the electronic inventory log. For example, a bag may be added to the inventory log at the time of collection upon filling and sealing the bag or upon entry into an inventory space. In one embodiment, a blood component collection machine wirelessly transmits data about each bag it fills.

In a preferred embodiment, each blood component in the blood center's inventory is tracked using radio frequency identification (RFID) technology. For example, in some embodiments, each blood component unit includes an RFID chip/tag on the bag. The RFID chip may be read by the blood component collection machine at the time of collection or by an RFID reader at the time the blood component bag is placed into storage in the blood center. Such a reading adds the blood component unit to the inventory log. The RFID chip may again be read when the blood component unit is removed from storage in the blood center or enters a health care facility. Such a reading may remove the unit from the inventory log. In other embodiments, the blood component unit is tracked electronically using a bar-code scanner. In such embodiments, each bag of blood component includes a bar-code uniquely identifying the unit of blood component.

In some embodiments of a blood component supply chain management system 100, software for the Blood Center Inventory Module 110 comprises a portion of the blood component supply chain management system software. In other embodiments, software and related hardware configured to track the blood center's inventory is provided separately. For example, in some embodiments, the blood component supply chain management system 100 is configured to be an open-platform that integrates with a blood center's existing inventory tracking software.

Returning to FIG. 1, some embodiments of a blood component supply chain management system 100 include a Health Care Facility Inventory Module 120. Such a module enables automated tracking of blood component units even after the units leave the control of the blood center, for example, once the units enter a health care facility. As described above, in various embodiments, each bag or other unit of blood component contains a tracking device, such as an RFID chip or barcode. Using said tracking device, in some embodiments, a unit's entry into a health care facility's inventory and exit from said inventory is tracked electronically when detected by an RFID reader or barcode scanner. The blood component unit's status is automatically updated in an electronic inventory log maintained for the health care facility. In various embodiments, the health care facility's inventory log at least includes a unique identifier, the component type, the blood type, and the expiration date for each blood component unit housed in the health care facility's inventory.

In various embodiments, the health care facility's inventory log is viewable by technicians and administrators of the health care facility and/or blood center personnel, enabling them to better track the inventory and identify when supplies are in excess, adequate levels, running low and/or when particular blood component units are nearing or have exceeded their expiration dates. The inventory log may display alerts, such as, for example, bolded or colored log entries, pop-up windows, or alert flags when one or more units are expired or almost expired.

Using the blood component supply chain management system 100 of some embodiments, health care facilities can directly and electronically order particular blood components as the needs arise. Additionally or alternatively, in some embodiments, health care facilities can set up the system such that orders for particular blood components are placed automatically by the system when current supplies fall below a specified amount. That specified amount may be a default amount determined by the system or specified by the health care facility. In some embodiments, health care facilities can store financial data in the system so that payments can be automated at the time of ordering.

Advantageously, in some embodiments, a blood center can monitor the inventory log of a health care facility. This allows the blood center to track a health care facility's supply and rate of usage, allowing the blood center to predict demand and identify real-time demand. Using such a system, a blood center can be alerted when a demand for more blood components exists, before the demand becomes critical. In various embodiments, a blood center provides blood components to tens or hundreds of hospitals and other health care facilities. Utilizing embodiments of the blood component supply chain management system 100, a blood center can track usage, current demand, and upcoming demand of its various customers individually or in an aggregate view.

The blood component supply chain management system 100 of FIG. 1 also includes a Recruitment Module 130. In various embodiments, the Recruitment Module 130 facilitates a blood center's recruitment efforts, particularly, for example, when a current or upcoming demand is identified by the system. The module may improve the efficiency of the recruitment processes. The module may automate all or portions of the recruitment process. Advantageously, in various embodiments, the Recruitment Module 130 identifies the best, or recommended, donors to recruit. Particularly when demand for a particular blood component exists or is imminent, blood centers would benefit from recruiting reliable donors capable of donating a maximum allowable amount of the particular needed blood component. Doing so would increase the speed at which a blood center can generate supply to fill demand. Thus, in some embodiments, the system analyzes the donor profiles of past donors, comparing the blood center's past donors along one or more metrics, to identify recommended donors. (Donor profiles are created for every donor, and the creation of such profiles is discussed in more detail below.)

Recommended donors (i.e., optimal donors) often have one or more of the following preferred characteristics: they have a desired blood type, they donated sufficiently in the past so as to be eligible to donate again, similarly, the number of times they donated within the past year is sufficient so as to be eligible to donate again, they have reliably showed up to past donation appointments for which they were scheduled; they meet current regulatory donation criteria for a particular needed blood component; and they are eligible to donate the particular needed blood component based on their gender, height, and weight. Optionally, in some but not all embodiments, the donors have successfully donated the particular needed blood component or other blood component in the past. In some embodiments, the system first identifies which of the blood center's past donors are currently eligible to donate. The eligible donors may then be compared and those with the largest number of desirable attributes selected as recommended donors.

In various embodiments, the Recruitment Module 130 works in conjunction with the Customer Relationship Management (CRM) Module 140 to facilitate the recruitment process. Once recommended donors are identified, the CRM may be utilized to identify contact information for the recommended donors and coordinate efforts for reaching out to the recommended donors. In some embodiments, the system, via the Recruitment Module 130 and/or the CRM Module 140 generates automated emails, text messages, automated phone calls, or other electronic communications, which are sent to the recommended donors to recruit them to donate again. The CRM Module of some embodiments additionally provides a platform through which blood center staff and/or donors can electronically schedule blood collection appointments. The platform may also allow blood drive organizers to electronically schedule blood drives, such as, for example, through a web-based or application interface.

In some embodiments, the CRM Module 140 is provided as a portion of a blood component supply chain management system 100. In other embodiments, CRM software is provided separately. For example, in some embodiments, the blood component supply chain management system 100 is configured to integrate with a blood center's existing CRM software.

Some embodiments of an blood component supply chain management system 100 also include a Schedule Review Module 150. In some embodiments, the Schedule Review Module 150 improves a blood center's ability to efficiently collect a particular blood component in current or imminent demand by making modifications to scheduled appointments as demand changes, so that the blood component that is ultimately collected is a blood component that is needed. In some embodiments, when a need arises for a particular blood component, the Schedule Review Module 150 allows blood center staff to identify donors with upcoming appointments who can help the blood center meet the changing needs. For example, the module of some embodiments reviews logs of scheduled appointments, identifies appointments that are for the collection of a blood component that is not in particular demand, and optionally, suggests modifications to the appointments such that a needed blood component is instead collected at the appointment optimizing the appropriate collection device technology. In some embodiments, the module first reviews a donor's profile to ensure the donor is eligible to donate a needed blood component.

The blood component supply chain management system 100 of various embodiments also includes a Donor Optimizer Module 160. Advantageously, the Donor Optimizer Module 160 facilitates real-time modifications in blood component collections to match real-time needs. Collection recommendations are provided to optimize the donor's potential based on defined criteria for the collection device technology. The module of some embodiments identifies donors on the day of donation, reviews the blood component the donor is scheduled to donate, and may suggest modifications if a demand for a blood component arises that is different than the blood component the donor is scheduled to provide or if the system detects that the scheduled collection is not optimized. In some embodiments, the suggested modification is presented to a user, such as a donor or a blood center staff member, at the time of collection. The Donor Optimizer Module 160 may integrate with an input device configured to receive an input from a donor, which uniquely identifies the donor. The Donor Optimizer Module 160 may also integrate with a blood collection device such that if a user selects to make a suggested modification, the blood collection device receives instructions to collect the appropriate blood component.

The blood component supply chain management system 100 of various embodiments further includes a Donor Profile Module 170. Past donors and scheduled donors have donor profiles stored in the blood component supply chain management system. A donor profile can be created and edited via the Donor Profile Module 170. In various embodiments, the donor profile is a donor-specific data space within the memory of the blood component supply chain management system, which is accessible using a unique identifier. The donor-specific data space stores data pertaining to the donor. The donor-specific data is maintained by the blood component supply chain management system and accessible by users with proper credentials, such as a specific donor, and optionally, blood center staff. The donor profile may include: biographical data such as a donor's birth date, gender, weight, height, and blood type; and appointment history such as a log of past donations, including dates and products donated, a count of past donations, a show rate (i.e., percent of scheduled appointments the donor appeared for), etc. The donor profile may be accessible via a web-based interface or application interface, for example, to enable review of historical collections and the characteristics of scheduled donors. In some embodiments, data pertaining to each donor's past appointments (e.g., show rate, date of donation, component type and amount donated, etc.) can be aggregated for each donor or for all individuals who donated to a blood center during a particular time interval. Storing and aggregating such information in the system allows for period reviews, such as, for example, quarterly compliance reviews. In some embodiments, the donor profile is automatically edited by the system, for example, when an appointment is scheduled, when an input device detects the arrival of the donor at a donation site, and when a blood collection device records a successful collection.

System Components

The various functionality described above is possible when implemented by a system formed of one or more computers, such as one or more servers coupled via a communication network to at least one or more tracking devices, one or more blood component collection devices, and one or more user workstations. One example of such a system is provided in FIG. 2 and discussed in detail below.

Figure 2:
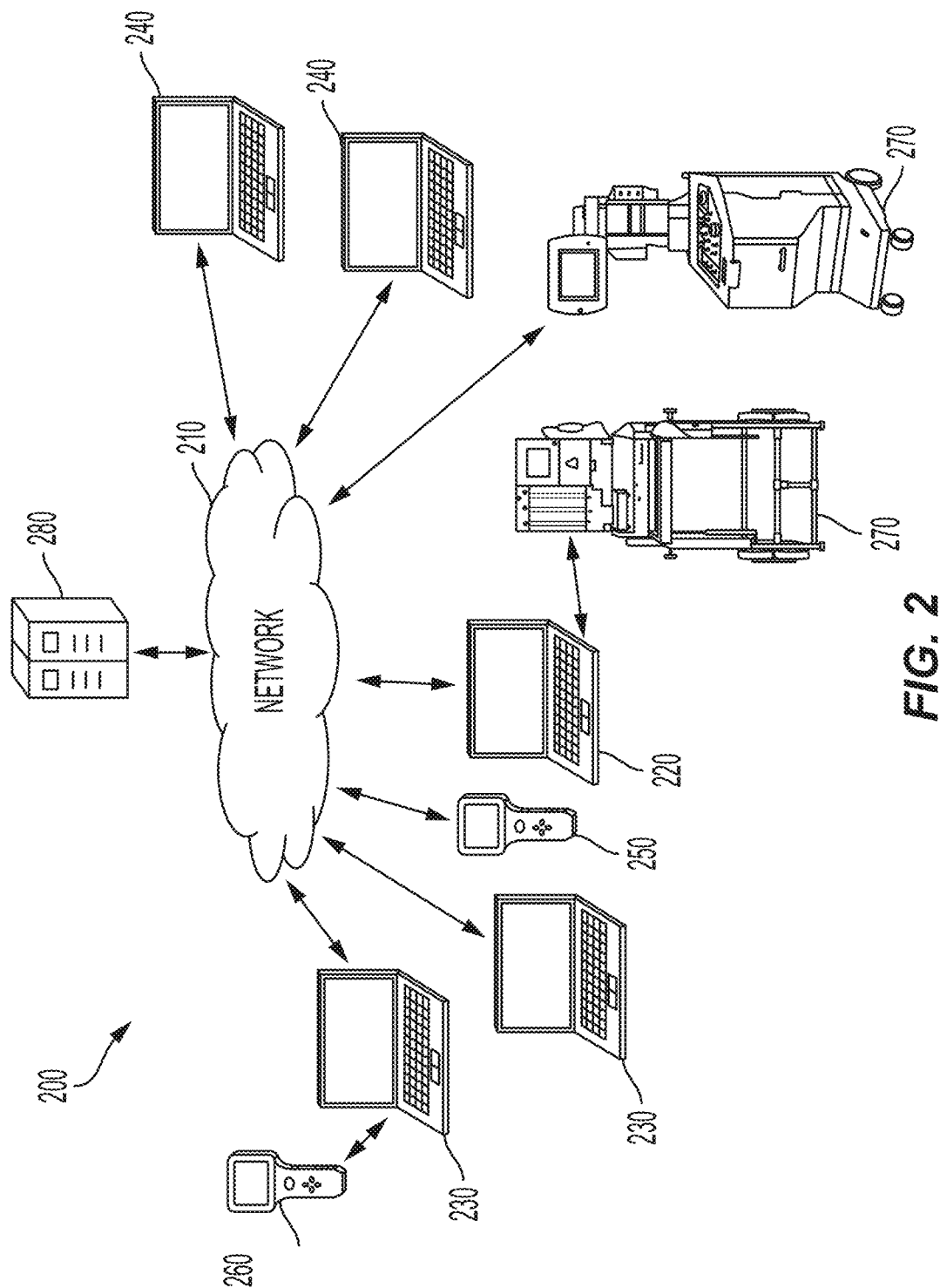
FIG. 2 is a schematic diagram of a blood component supply chain management system, depicting various components of the system and interactions between the components in accordance with another exemplary embodiment.

Specifically, FIG. 2 illustrates a schematic diagram of the hardware components found in one embodiment of an blood component supply chain management system 200 and includes a schematic illustration of the interactions between said components. One skilled in the art will appreciate that the embodiment is illustrative in nature only and various components may be added, deleted, or substituted and various different hierarchies and modes of communication between the devices may be employed. In the depicted example, the blood component supply chain management system 200 is formed of a plurality of computerized devices. The system 200 includes a communication network 210 through which some or all of the various devices communicate with one another. In some embodiments, a plurality of the devices are configured to transmit information to, and receive information from a server 280 via the communication network 210. The network can be a local area network (LAN) or a wide area network (WAN). In some embodiments, the network is a wireless communication network to which at least some of the devices are connected, such as, for example, a mobile WiMAX network, LTE network, Wi-Fi network, or other wireless network. In other embodiments, the communication between at least some of the system devices and the server 280 occurs over the interact via a wired network, such as a DSL cable connection, or over Ethernet or an intranet.

In various embodiments, the system is accessible to users of the system via user workstations, such as workstations at a blood center 220, workstations at various health care facilities 230, and donor workstations 240. The workstations may be specialized computers configured solely for connection to the system 200, or they may be generalized computers made to perform specialized functions through its connection to the system 200. For example, in some embodiments, the various workstations 220, 230, and 240 are desktop computers, laptop computers, and/or mobile devices such as tablets or smartphones.

In various embodiments, the blood component supply chain management system 200 is owned, operated, or managed by, or otherwise tailored to, an individual blood center and/or health care facility. The system may enable a blood center to track its own inventory as well as the inventory of its customers and recruit, schedule, and manage communications and relationships with donors and potential donors. Additionally or alternatively, the system may enable health care facilities to track their own respective inventories. In some embodiments, each health care facility utilizing the system may additionally be able to view the inventory levels of the system-affiliated blood center. In various embodiments, each network includes one connected blood center and a plurality of connected health care facilities and donors. It will be appreciated though that a single blood center may have a plurality of blood center workstations 220 connected to the system. Thus, while one or two workstations are depicted for each participant, it will be appreciated that the system 200 may include any number of workstations 220, 230, and 240. The system 200 may also include any number of tracking devices 250, 260 and blood collection devices 270, which are described in more detail below.

In various embodiments, the server 280 includes a processor and memory, and software code is stored in the memory, which, when executed by the processor, causes the system to perform some or all of the system functions described above. In some embodiments, the server 280 includes an application server. In some such embodiments, some software code is stored in the server 280, while additional software code is stored on each other network-connected device (e.g., 220, 230, 240, 250, 260, 270) in the form of a program application. In some such embodiments, "back end" functions such as storing information sets in databases, calculations, analyses, and information retrieval is largely performed by, and coded for, within the server 280, while "front end" functions, such as the display of information on a graphical user interface (GUI), is performed by, and coded for, within the other network-connected devices. Additionally or alternatively, in some embodiments, the server 280 includes a web server and various features and functionality are made possible by the software code stored within the server 280. In some such embodiments, each user workstation 220, 230, 240 may include an internet browser, through which users can access, and interact with, the blood component supply chain management system 200. In various embodiments, the server 280 also includes a database server on which information sets such as inventory logs, scheduling logs, and donor profiles are stored. It will be appreciated to one skilled in the art that the server 280 may be formed of any suitable number of servers. For example, in some embodiments, the server 280 includes one or a plurality of application servers, one or a plurality of web servers, and/or one or a plurality of database servers.

In some embodiments, the blood component supply chain management system 200 includes a blood center subsystem and a health care facility subsystem. In such embodiments, the devices affiliated with the blood center subsystem, for example, workstations 220 and 240, tracking devices 250, and blood collection devices 270, connect to one or more other blood center devices and/or one or more blood center servers. Similarly, the devices affiliated with the health care facility subsystem, for example, workstations 230 and tracking devices 260, connect to one or more other health care facility devices and/or one or more health care facility servers. In various embodiments, the blood center servers and health care facility servers are communicatively connected such that information can be exchanged between the blood center subsystem and the health care facility subsystem.

As depicted in FIG. 2, the various devices of the system interact with the network 210, and accordingly, each other, via a two-way (forward and reverse) communication link. The devices each include input/output devices for wired communication connections (e.g., modems, network cards, external data buses, ports, etc.) and/or wireless receivers and transmitters, which allow each device to transmit and receive information. Exemplary information exchanged by the various components is described in more detail below. These are examples only, and various other information exchanges are conceived and expressly contemplated herein.

In certain embodiments, the blood center workstation 220 has an input/output device (e.g., mouse, keyboard, touchscreen, monitor, etc.) allowing it to receive inputs from a user and display graphical outputs. Users, such as blood center staff, may enter information about the blood center's inventory, scheduling information, or information about new or potential donors. Such information is transmitted to the server 280 via the communication network 210 for storage, and optionally, for processing. Blood center staff can also use the blood center workstations 220 to send requests for, and receive, information such as: data regarding the inventory of various health care facilities, stored donor profiles, stored donor contact information, stored scheduling data, orders from health care facilities for additional blood components, and a summary of the greatest demands for blood components and/or upcoming demands, as determined by the system from various health care facility inventories.

The health care facility workstations 230 also have input/output devices (e.g., mouse, keyboard, touchscreen, monitor, etc.) for receiving inputs from users and displaying graphical outputs to users. The workstations 230 may receive inventory information, which it presents to a user via a GUI. By sending and transmitting data, the health care facility workstations 230 enable users to edit health care facility inventory data and view such inventory data in a number of formats. For example, users may be able to view a list of all units in the health care facility's inventory, view details about the supply of a particular blood component, and view alerts and warnings generated by the system. Using the health care facility workstations 230, health care facility staff may also be able to transmit orders for more blood components, as well as billing or payment information. In some embodiments of the system, health care facility staff may also be able to view the current inventory available at a blood center.

Similarly, donor workstations 240 also have input/output devices (e.g., mouse, keyboard, touchscreen, monitor, etc.) for receiving inputs from users and displaying graphical outputs to users. Upon request by a user through interaction with, and data input via, a GUI, the workstations 240 may receive scheduling and donor profile information stored in the server 280. Such information may be displayed to the user for review and/or editing. The workstations 240 may also transmit scheduling and/or donor profile data to the server 280 in order to add to, or update, the stored information.

As shown in FIG. 2, the system may include a plurality of tracking devices, such as the blood center tracking device 250 and the health care facility tracking device 260. Each party may have one or more tracking devices to track its inventory. In some embodiments, the tracking device 250, 260 is an RFID reader or computer kiosk including an RFID reader; in other embodiments, it may be any other suitable tracking device, such as a barcode scanner. In some embodiments, the tracking devices are electrically or wirelessly connected to a network-connected computer. For example, for illustration purposes, the health care facility tracking device 260 of FIG. 2 is connected to the health care facility workstation via a cable or a wireless connection such as Bluetooth® or other radiofrequency connection. In such embodiments, the workstation 230, which is connected to the tracking device 260 and the network 210, transmits detected changes in inventory to the server 280. In other embodiments, the tracking device itself includes a wireless transmitter and is configured to transmit detected inventory data to the server 280 via the network 210 (see, for example, tracking device 250).

Similarly, the system may include a plurality of blood collection devices 270, such as, for example, one or more of the Alyx®, CompoGuard®, Aurora, and/or Amicus® devices. These devices may collect whole blood and/or certain blood components. In some embodiments, such devices 270 are configured for wireless communication and include a wireless receiver and transmitter. The blood collection devices 270 of various embodiments may exchange data with the server 280 via the network 210. Additionally or alternatively, a blood collection device 270 may exchange data with a blood center workstation 220 via a wired or wireless connection, and the blood center workstation 220 may exchange such information with the server 280. In various embodiments, the exchange of data between one or more blood collection devices 260 and one or more workstations 220 or servers 280 enables blood centers to: send the collection devices 270 instructions regarding what components to collect, monitor machine and operator performance, and/or capture and analyze procedure data remotely.

Figure 3:
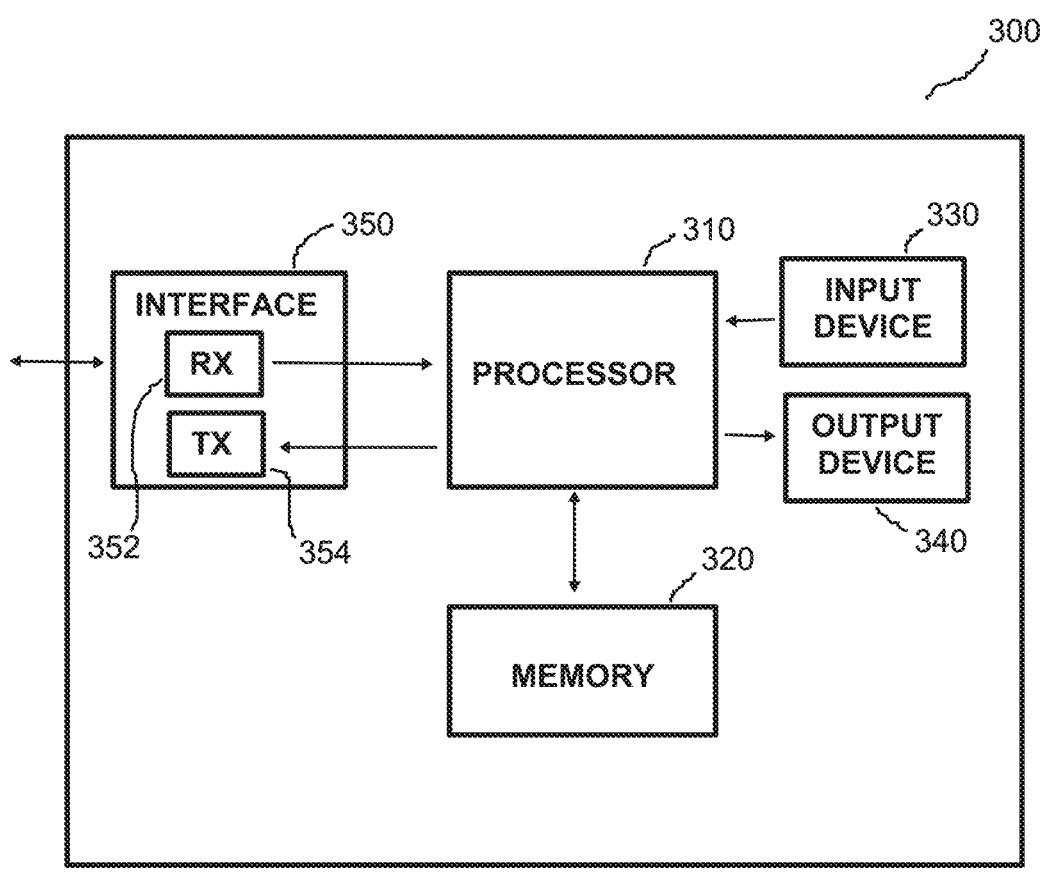
FIG. 3 is a general schematic block diagram of a blood component supply chain management system in accordance with another exemplary embodiment.

In another embodiment of the blood component supply chain management system, the system is formed of a server. The server of such embodiments is configured to receive information from, and send information to, various remote components, and is further configured to store data and execute stored instructions, enabling the system to perform some or all of the inventory optimization functions and methods described herein. A functional block diagram of one such embodiment of the blood component supply chain management system is depicted in FIG. 3 and described below. Although the functional blocks in FIG. 3 are depicted and described separately, it will be appreciated by one skilled in the art that functional blocks need not be separate structural elements. Multiple functional blocks may be implemented by a single structural element; alternatively, any single functional block may be implemented by a plurality of structural elements. For example: the memory described below may be a storage device coupled to a processor and/or may be integral to the processor. For example, an ASIC may comprise both the processor and the memory.

The blood component supply chain management system 300 of FIG. 3 includes: memory 320 configured to store data and instructions; a processor 310 configured to execute the instructions stored in memory to implement an operating system and various system functions; and a communication interface 350 configured to receive information from, and transmit information to, remote devices.

The processor 310 can be a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. The processor 310 may also be implemented as a combination of computing devices, e.g., a combination of a DSP and a microprocessor, a plurality of microprocessors, one or more microprocessors in conjunction with a DSP core, or any other such configuration.

The processor 310 is coupled to memory 320 via a system bus, which enable the processor to read information from, and write information to, memory 320. In various embodiments, the system bus couples various components of the system and enables data and signals to be exchanged between the components. The system bus may operate on any of a number of known protocols. Additionally or alternatively, the processor 310 may contain memory, such as processor registers.

The memory 320 stores a set of instructions, in the form of software code, which the processor 310 is configured to execute. Additionally, the memory may be configured to store data received from remote devices via the communication interface 350. The memory 320 can include processor cache, including a multi-level hierarchical cache in which different levels have different capacities and speeds. The memory may include random access memory (RAM), read only memory (ROM), or preferably, both. ROM may store a basic input/output system (BIOS) or other basic operating information system, while RAM generally stores the operating system (OS), application software, and data. Alternatively or additionally, the memory may include flash memory, electrically programmable ROM (EPROM), and/or electrically erasable programmable ROM (EEPROM). The storage devices can also include a disk drive, for example, a hard disk drive. Other volatile or non-volatile storage devices may additionally or alternatively be used, including optical discs, floppy discs, magnetic tape, and Zip drives.

The processor 310, in conjunction with software stored in the memory 320, executes an operating system, such as, for example, a Windows, Unix, Mac OS, or Solaris operating system. The processor 310 also executes software applications stored in the memory 320. The software applications may include code written in any suitable programming language known to those skilled in the art, including, for example, Java and C++ programming languages. In some embodiments, the memory 320 includes software for operating the blood component supply chain management system 300 as a web server. For example, the memory 320 may include software provided by Apache or Tomcat. In some embodiments, the memory 320 includes a network-accessible database, which is accessible to remote devices via the network interface 350. For example, software provided by Oracle or IBM may be stored in the memory 320, providing database services to the processor 310 and to users of the blood component supply chain management system 300.

The network interface 350 to which the processor 310 is coupled, via, for example, the system bus, includes both a receiver 352 and a transmitter 354. In some embodiments, the receiver 352 and transmitter 354 are separate components; in other embodiments, they form part of the same component, such as a transceiver. In various embodiments, the transmitter 354 and network interface 350 prepare data generated by the processor 310 for transmission over a communication network according to one or more network standards. The receiver 352 and network interface 350 demodulate data received over the communication network according to one or more network standards.

Optionally, in some but not all embodiments, the blood component supply chain management system 300 includes one or more input devices 330 and/or output devices 340 coupled to the processor 310. Such devices may enable a system administrator to enter inputs into, and receive outputs from, the system 300. Input devices may include, for example, a keyboard, mouse, touchscreen, button, switch, and/or microphone, and output devices may include, for example, a display, printer, or speakers.

Methods

Using some or all of the devices, components, and systems described above, various methods may be implemented by the blood component supply chain management systems. Such methods may integrate into existing supply chain processes and improve the efficiency, predictability, and/or outcomes of the blood component supply chain. Various embodiments of the methods performed by blood component supply chain management systems include methods for tracking blood component inventories, forecasting blood component demand, and coordinating optimized donations to meet current and anticipated demand. Some systems perform all such functions together in an integrated manner. Other systems may perform only one or some of the inventory optimization methods.

Figure 4:
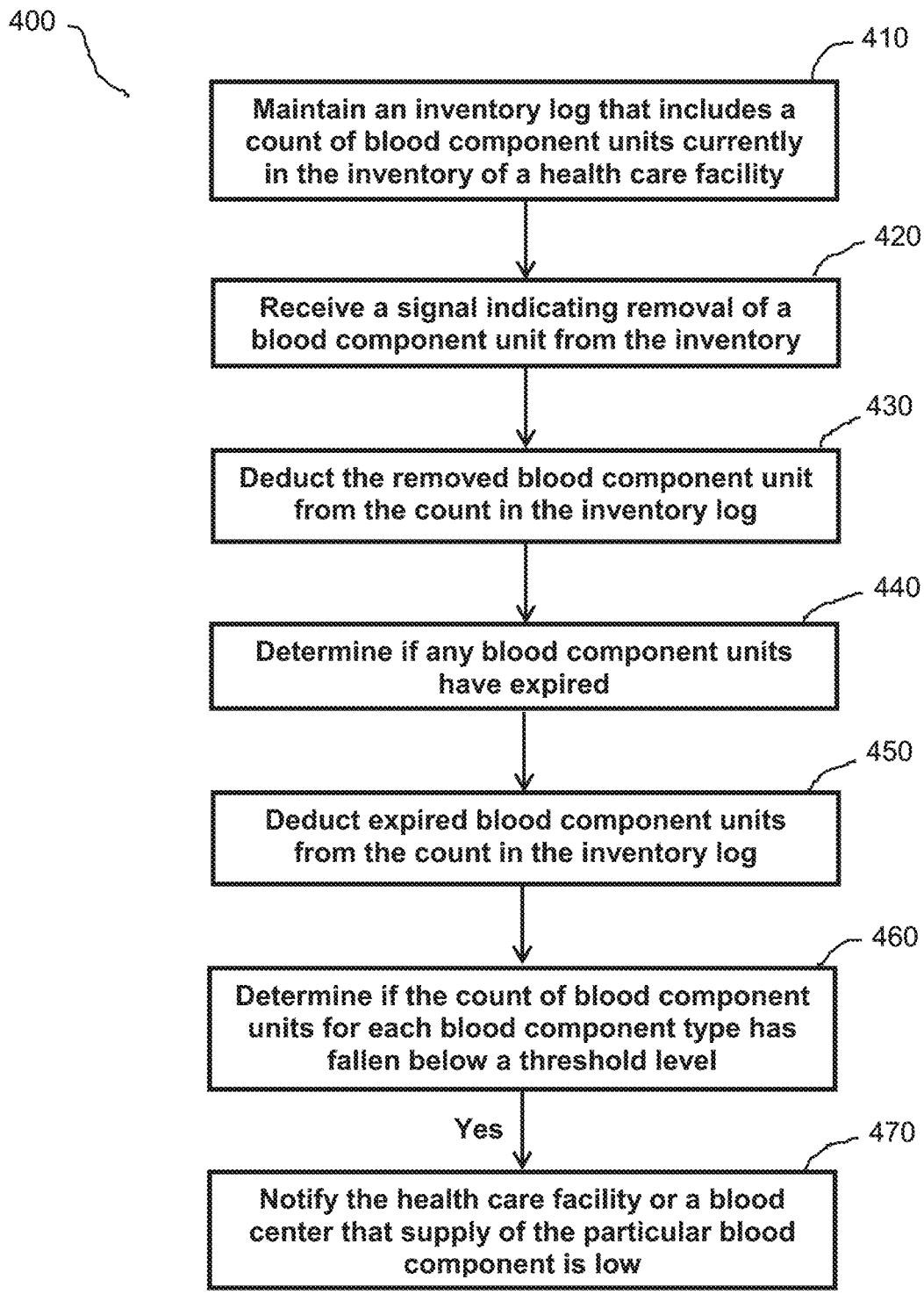
FIG. 4 is a flow chart illustrating a method of tracking current blood component inventory in a blood component supply chain in accordance with another exemplary embodiment.

In one embodiment, a method for optimizing inventory includes a method for tracking current blood component inventory in a blood component supply chain. One such embodiment is depicted in FIG. 4. In the illustrated embodiment, the blood component supply chain management system maintains an inventory log for a health care facility, as shown at block 410. The inventory log includes a count of blood component units currently in the health care facility. One of skill in the art will appreciate that a health care facility may have a log recording the inventory within one storage location within the health care facility, a plurality of logs recording the inventory within a respective plurality of storage locations within the health care facility, or one log recording the inventory throughout various locations within the entire health care facility. Moreover, one of skill in the art will appreciate that while the inventory log of a single health care facility is described herein, the system may include inventory logs for tens or hundreds of health care facilities served by a blood center. The count within each inventory log may include a total count and a count for each component type/blood type combination. For example, the inventory log may list the number of all blood component units in a health care facility inventory, as well as the number of A-type platelets, AB-type platelets, A-type plasma, AB-type plasma, O-type red cell, etc. The log includes identification data, such as, for example, a unique identifier, a component type, a blood type, and an expiration date, for each blood component unit.

As shown at block 420, in some embodiments, the system receives a signal, such as a signal from an RFID reader, indicating removal of a blood component unit from the health care facility inventory. In one non-limiting example, an RFID reader is placed at the entrance of a blood component storage room. When a unit is removed from the room, it is detected by the RFID reader, which transmits appropriate signals to the system server or a network-connected health care facility workstation. In another non-limiting example, an RFID reader is placed within a blood component storage room, and the contents of the room are interrogated regularly, for example, once a day. The resulting signals implicitly indicate when a blood component unit has been removed from the inventory. In other embodiments, the signals are received by the system directly or indirectly from a barcode scanner, which scans a barcode on a unit of blood component at the time the unit is removed from inventory. In some embodiments, additional information is recorded at the time of blood component removal including, for example, who is removing the inventory, where the removed inventory is being taken, and which patient is receiving the removed inventory.

The system also receives a signal or user input when a blood component unit is added to the inventory. This may occur, for example, when an RFID reader placed within a blood component storage room interrogates the contents of the room regularly, thus detecting any additions or subtractions to the inventory. In another embodiment, a blood center maintains an inventory log of its own blood center inventory. When a unit of blood component is removed from the blood center inventory and delivered to a health care facility, the blood center may input data indicating the receiving health care facility. Such an input may be received by the system as a signal indicating addition of a unit to the receiving health care facility's inventory.

In various embodiments, as shown at block 430, the system increments a health care facility's inventory log when a unit of blood component is added to the inventory and deducts the unit of blood component from the health care facility's inventory log when the unit is removed from the inventory.

Additionally or alternatively, as shown at block 440, the blood component supply chain management system may search the inventory log of a health care facility to determine if any blood component units have expired or are nearing expiration. Expired blood component units may be deducted from the count of blood component units in the inventory log, as shown at block 450. In some embodiments, the inventory log includes a total count and a fresh/safe-to-use count. The total count indicates the total number of blood component units in the health care facility's inventory, and the fresh/safe-to-use count indicates the number of blood component units still safe for use. Thus, in such embodiments, expired units will remain present in the total count but will be removed from the fresh/safe-to-use count. In some embodiments, the system will generate an alert identifying blood component units that are expired or expiring soon. Additionally or alternatively, in some embodiments, the blood component supply chain management system may search the inventory log of a health care facility to determine if any blood component units have been quarantined or recalled. In some such embodiments, quarantined and recalled blood component units will appear in the total count but not in the separate fresh/safe-to-use count. In some embodiments, the inventory log will list or otherwise identify the location of all units, for example, so that fresh units are easily accessible when needed for a patient and expired, quarantined, and/or recalled units can be readily located and handled properly. In some embodiments, a flag or other electronic alert will be generated within the electronic inventory log when a blood component unit is quarantined or recalled.

At block 460, the system compares the count of units of a particular blood component to a set threshold level to determine whether the count of blood component units for a particular blood component has fallen below a threshold level. The system may compare the total count or the fresh/safe-to-use count to the set threshold level. The threshold level may be a default level set by the system or a level entered by the health care facility or blood center.

If the count has fallen below a threshold level, the system moves to block 470 in which the system notifies the health care facility and/or the blood center that supply of a particular blood component is low. The notification may be, for example, a pop-up alert viewable on a display at a workstation or an automated phone call, email, or text message. Such a method may enable health care facilities and blood centers to better track the usage patterns and inventories of health care facilities. If the count is above the threshold level, the system moves back to block 410.

In some embodiments, once the count has fallen below a threshold level, an order for additional supplies is automatically placed by the system. Payment may also be automatically handled by the system. For example, in some embodiments, payment is made at the time an order for blood component units is placed. In other embodiments, payment is made at the time an order of blood component units is shipped. In other embodiments, payment is made at the time a blood component unit is removed from the health care facility's inventory. In some embodiments, payment information for the health care facility is stored within the system memory such that a credit card is automatically billed or money from a cash account is automatically deducted at the time payment is due. In other embodiments, the health care facility placing an order for blood component units is prompted for payment information at the time of ordering.

Figure 5:
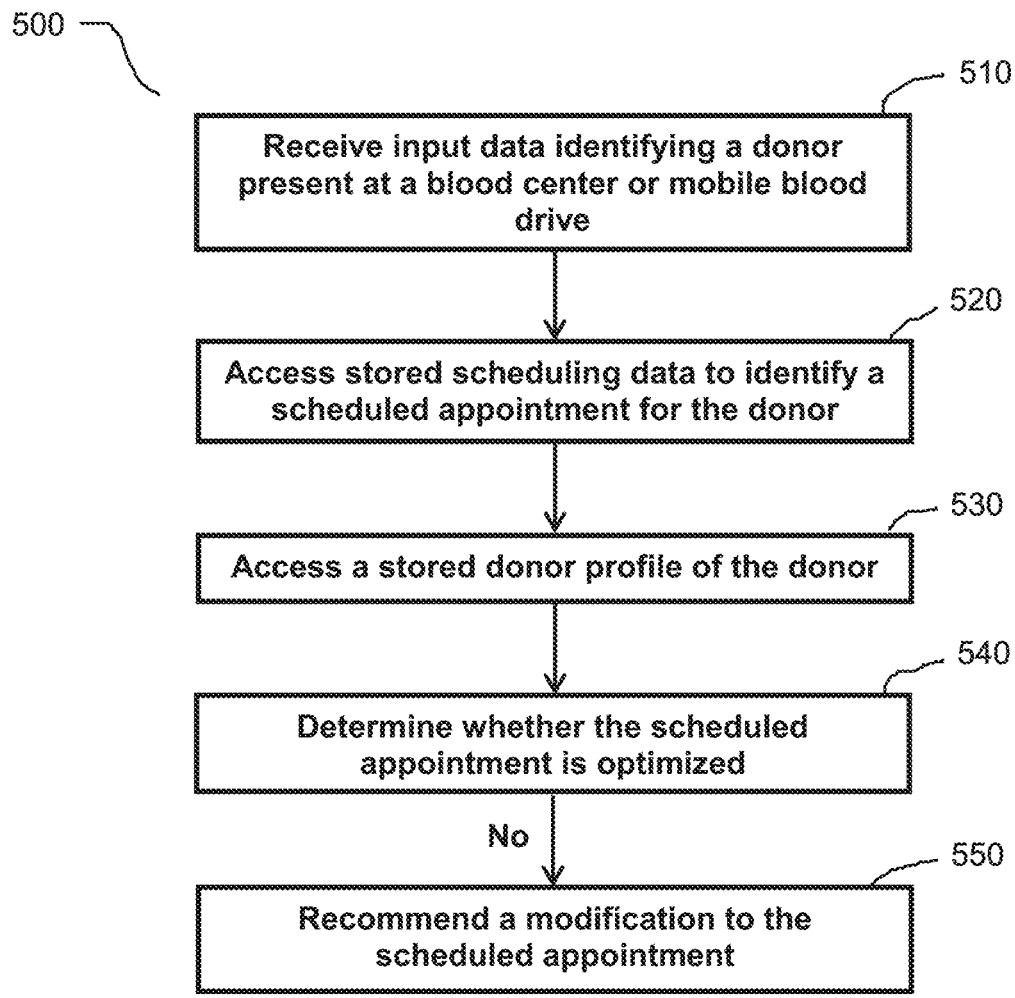
FIG. 5 is a flow chart illustrating a method of generating new blood component inventory to address anticipated or current demand in a blood component supply chain in accordance with another exemplary embodiment.

FIG. 5 depicts one embodiment of a method for generating new blood component inventory. Such a method helps coordinate new collections of blood components to better address anticipated or current demand in a blood component supply chain. As shown at block 510, in some embodiments, the blood component supply chain management system receives input data identifying a donor who presents himself or herself at a blood center or mobile blood drive. Upon arriving for blood donation, a donor may scan a donor-specific card or badge, which has identification information stored thereon, for example, in a magnetic strip, RFID tag, or barcode. Alternatively, the donor may be identified through biometric inputs such as a fingerprint or retinal scan. In other embodiments, the donor may enter donor-specific identification credentials such as a username, login ID, password, and/or pin into a blood center workstation to verify the donor's identify.

At block 520, the system pulls up the donor's current appointment information by accessing scheduling data stored in a system database. At block 530, the system pulls up the donor's donor profile which is also stored in, and accessed through, a system database.

At block 540, the system determines, at least in part from the scheduling data and the donor profile, whether the scheduled appointment is optimized. Donation optimization considerations include, for example, whether a donor is scheduled to donate the maximum number of blood components the donor is qualified to donate based on, for example, past donation history, the donor's current biographical information, and device opportunities. In some embodiments, the scheduled appointment is optimized if: the scheduled blood component is a needed blood component for which there is current or anticipated demand, and a donation potential of the present donor is maximized. Thus, in some embodiments, the system identifies one or more blood components for which demand exists or is imminent. This may be done, for example, by implementing the method of FIG. 4. Alternatively, a health care facility staff member or blood center staff member may enter an input indicating which blood components are needed.

The one or more needed blood components are then compared to the blood component or components which the donor is scheduled to donate. The system may determine that the scheduled appointment is not optimized if the donor is not scheduled to donate a needed blood component but is eligible to donate such a product. Additionally, the system may assess, based for example, on the donor's gender, height, weight, and past donation history, whether the donor is able to donate more than he or she is scheduled to donate. For example, a donor may be scheduled to donate platelets, and to optimize the donation opportunity, the system will indicate the recommended number of treatment doses (i.e., the maximum safe number of doses) to collect, or the system may recommend an alternate collection type based on donor parameters, donation history, device opportunity, and inventory need. Similarly, a donor may be scheduled to donate Whole Blood when a double RBC donation and/or RBC and plasma donation is possible. In such a situation, the system may recommend a change in the appointment from Whole Blood collection to double RBC collection if the need for RBCs is greatest. The system may determine the scheduled appointment is not optimized if the donor is not scheduled to donate the maximum volume or number of products allowable.

At block 550, the system recommends a modification to the scheduled appointment if the appointment is not optimized. In some embodiments of the method, recommending a modification to the scheduled appointment includes suggesting that collection of the scheduled blood component be either substituted with collection of the needed blood component or supplemented with collection of the needed blood component or an additional blood component. Various potential, recommended modifications to the collection may be presented to the donor or a blood center staff member prior to collection. Such a recommendation may need to be approved by a staff member and consented to by the donor. In one embodiment, the recommendations are presented on a touchscreen along with the currently scheduled collection regimen. The health staff member and/or donor may select the desired collection regimen. In some embodiments, a blood collection device will automatically begin the appropriate collection upon selection of the desired collection regimen. In other embodiments, the health staff member will set up the blood collection device to begin the appropriate collection.

Figure 6:
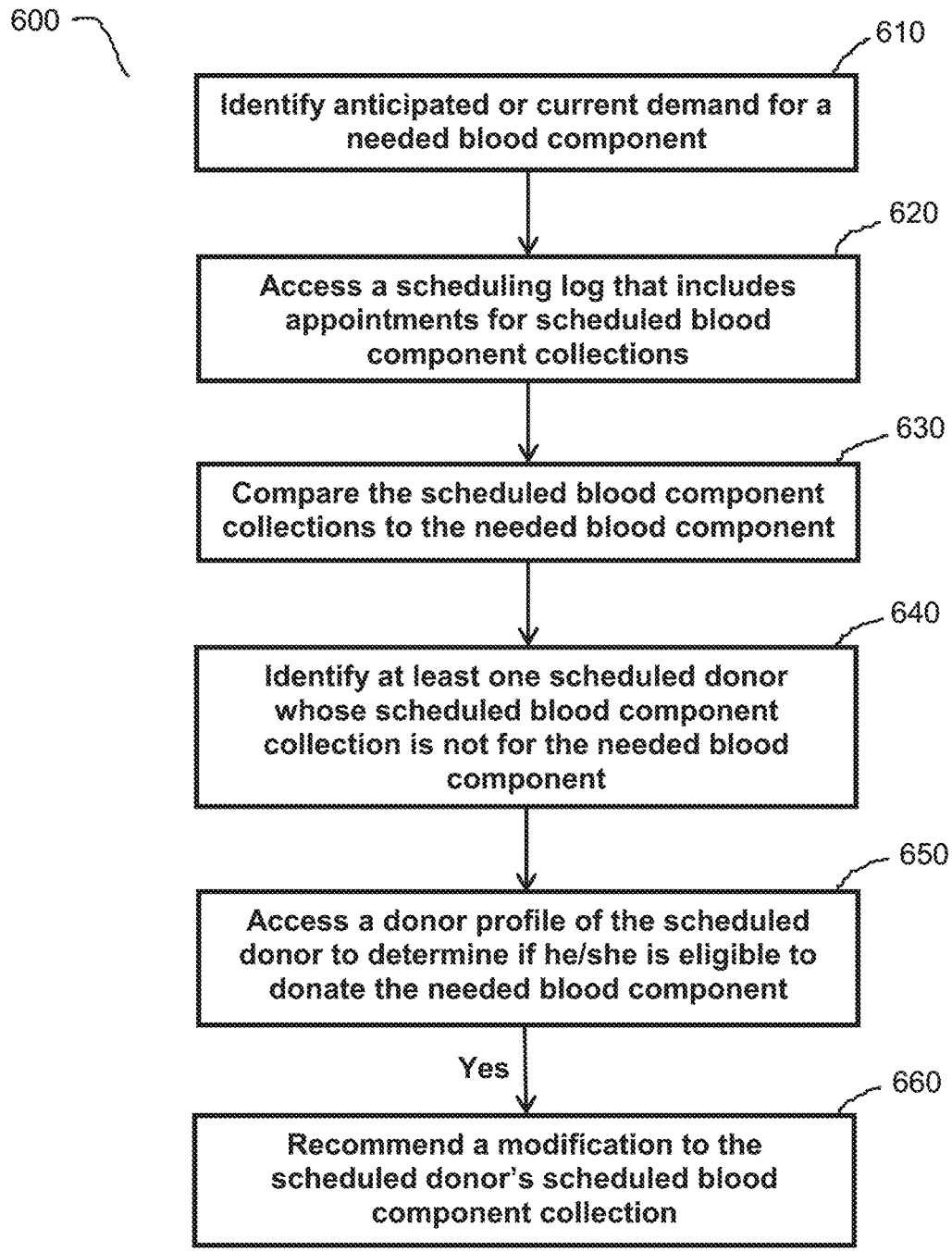
FIG. 6 is a flow chart of a method of generating new blood component inventory to address anticipated or current demand in a blood component supply chain in accordance with another exemplary embodiment.

FIG. 6 illustrates another embodiment of a method for generating new blood component inventory. Such a method 600 may be performed by a system in conjunction the method of FIG. 5 or independently. At block 610, the system identifies anticipated or current demand for one or more particular blood components. A blood component is referred to herein as a needed blood component when a current or imminent demand is determined to exist. The system may identify such demand by receiving an appropriate user input, such as an order for a blood component. Alternatively, the system may identify such demand by employing a method such as the method of FIG. 4.

At block 620, the system accesses a scheduling log from a system database. The scheduling log includes appointments for scheduled blood component collections. The system compares the scheduled blood component collections to the needed blood components in order to identify at least one scheduled donor whose scheduled blood component collection is not for a needed blood component, as shown at blocks 630 and 640.

In some embodiments, and as shown at block 650, the system accesses the donor profiles stored in the system's database for each of the scheduled donors whose scheduled blood component collection is not for a needed blood component. The system reviews the biographical information and donation history stored in each donor profile to determine whether a scheduled donor is eligible to donate a needed blood component. For example, to be eligible, a scheduled donor of a particular gender must meet the device criteria, for example, for double RBC donations, the scheduled donor must meet hemoglobin count, height, and weight requirements; moreover, a specified amount of time must have passed since the scheduled donor last donated. At block 660, the system recommends a modification to the scheduled donor's scheduled blood collection if the scheduled donor is eligible for a modification.

Figure 7:
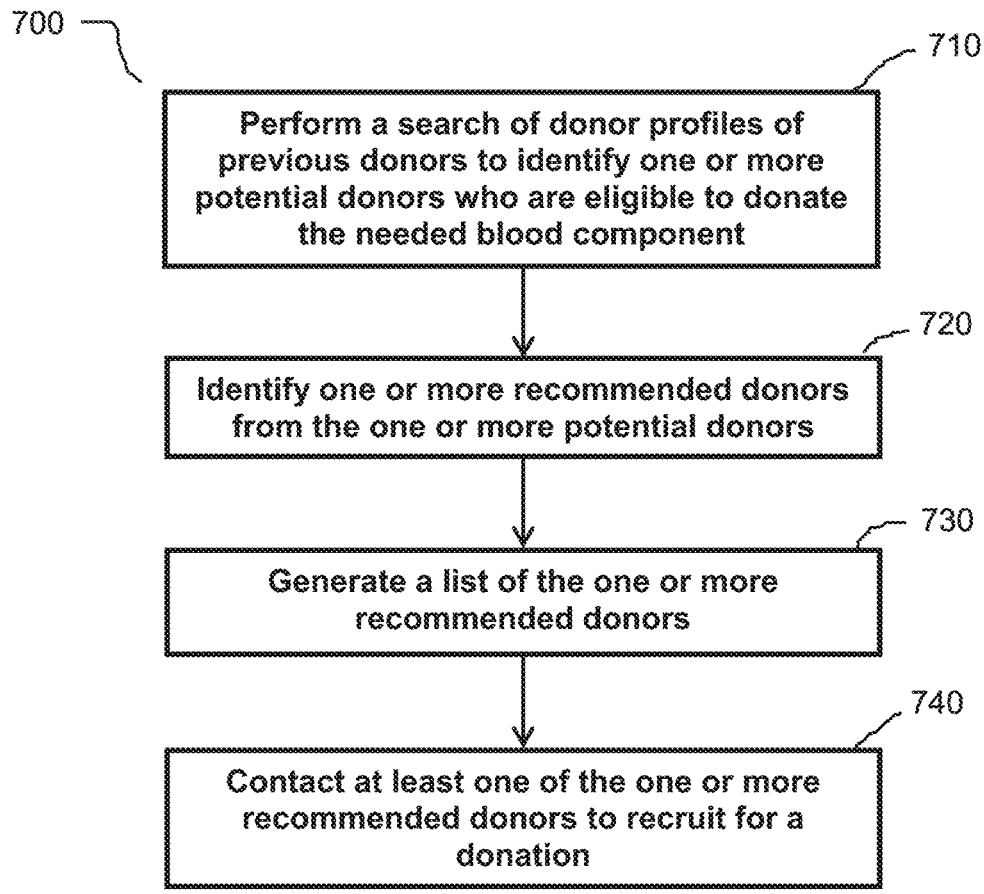
FIG. 7 is a flow chart illustrating a method of generating new blood component inventory to address anticipated or current demand in a blood component supply chain in accordance with another exemplary embodiment.

FIG. 7 is a flow chart illustrating another embodiment of a method for generating new blood component inventory in order to address anticipated or current demand in a blood component supply chain. A system employing the method 700 of FIG. 7 performs a search of donor profiles of previous donors to identify one or more potential donors, as shown at block 710. A potential donor is an individual who is eligible to donate the needed blood component. In some embodiments, the eligibility of a previous donor is based, at least in part, on one or more of the following characteristics of the previous donor: date of last donation, quantity donated within a given time period, number of times donated within a given time period, existence of past unsuccessful donation attempts, gender, height, weight, health status, health conditions, and blood type.

At block 720, the system identifies one or more recommended optimized donors from the potential donors. The one or more recommended optimized donors are also identified based, at least in part, on an assessment of each of their past show rates and successful collection rates. The system may generate a list of these recommended donors, as shown at block 730.

In some embodiments, contact information is obtained for one or more of the recommended donors, for example, by pulling the contact information from the corresponding donor profile or from an integrated CRM-managed database.

In some embodiments, the system contacts at least one or the recommended donors to recruit for a optimized donation, as shown at block 740. For example, the system may generate an automated phone call, text message, or email. In other embodiments, a blood center staff member may contact one or more of the recommended optimized donors from the list of recommended optimized donors generated by the system.

Employing various methods, such as, for example, the methods of FIGS. 5, 6, and 7, a blood component supply chain management system can modify a scheduled donation at the day of collection or in advance of the donation and can also recruit new donors for a particular blood component in order to meet upcoming or current demands in a blood component supply chain. The blood component supply chain management system can be a single system for all types of blood components or can be specific to a single type of blood or a single type of blood components.

Although the foregoing has included detailed descriptions of some embodiments by way of illustration and example, it will be readily apparent to those of ordinary skill in the art in light of the teachings of these embodiments that numerous changes and modifications may be made without departing from the spirit or scope of the appended claims.

The invention claimed is:

1. A system for collecting and tracking blood components, the system comprising a memory storing instructions and a plurality of processors executing the instructions, the instructions comprising:
    receiving biometric inputs at a workstation of a blood center to identify a donor;
    accessing, based on the identifying, a scheduled appointment for the donor including an identification of a scheduled blood component to be collected from the donor;
    accessing a user profile of the donor;
    determining, from the user profile, an eligibility for the donor based on unsuccessful donation attempts of the donor in past;
    determining based on a number of times the donor donated in the past, that the donor is eligible to donate again;
    determining, in real-time, that a need for desired blood components desired by the blood center is greater than that for the scheduled blood component;
    determining a device capability of a blood component collection machine in collecting the desired blood components during the scheduled appointment;
    modifying the scheduled appointment based on the determined eligibility, the determined need and the determined device capability;
    transmitting the modification for display at the workstation;
    automatically beginning the collecting of the desired blood components, using the blood component collection machine, upon selection of the desired blood components;
    reading, using the blood component collection machine, an RFID chip at a time of the collecting of the desired blood components;
    adding, based on the reading, the desired blood components to an electronic inventory log;
    reading, using the blood component collection machine, the RFID chip when the desired blood components are removed from storage in the blood center to automatically update a status of the desired blood components in the electronic inventory log;

determining, using the electronic inventory log, respective ones of the desired blood components that have been quarantined or recalled;
identifying a location of the respective ones of the desired blood components when the respective ones of the desired blood components have been quarantined or recalled; and
displaying an alert using the electronic inventory log, when the respective ones of the desired blood components are quarantined or recalled.

2. The system of claim 1, wherein the instructions further comprise determining and recommending a maximum safe collection amount.

3. A method for collecting and tracking blood components, the method comprising:
receiving, by one or more processors, biometric inputs at a workstation of a blood center to identify a donor;
accessing, by the one or more processors, based on the identifying, a scheduled appointment for the donor including an identification of a scheduled blood component to be collected from the donor;
accessing, by the one or more processors, a user profile of the donor;
determining, by the one or more processors, from the user profile, an eligibility for the donor based on unsuccessful donation attempts of the donor in past;
determining, by the one or more processors, based on a number of times the donor donated in the past, that the donor is eligible to donate again;
determining, in real-time by the one or more processors, that a need for desired blood components desired by the blood center is greater than that for the scheduled blood component;
determining, by the one or more processors, a device capability of a blood component collection machine in collecting the desired blood components during the scheduled appointment;
modifying, by the one or more processors, the scheduled appointment based on the determined eligibility, the determined need and the determined device capability;
transmitting, by the one or more processors, the modification for display at the workstation;
automatically beginning, by the one or more processors, the collecting of the desired blood components, using the blood component collection machine, upon selection of the desired blood components;
reading, by the one or more processors, using the blood component collection machine, an RFID chip at a time of the collecting of the desired blood components;
adding, by the one or more processors, based on the reading, the desired blood components to an electronic inventory log;
reading, by the one or more processors, using the blood component collection machine, the RFID chip when the desired blood components are removed from storage in the blood center to automatically update a status of the desired blood components in the electronic inventory log;
determining, by the one or more processors, using the electronic inventory log, respective ones of the desired blood components that have been quarantined or recalled;
identifying, by the one or more processors, a location of the respective ones of the desired blood components when the respective ones of the desired blood components have been quarantined or recalled; and
displaying, by the one or more processors, an alert using the electronic inventory log, when the respective ones of the desired blood components are quarantined or recalled.

4. The method of claim 3, further comprising:
performing, by the one or more processors, a search of user profiles of previous donors to identify potential optimized donors who are eligible to donate one or more of the desired blood components;
identifying, by the one or more processors, one or more recommended optimized donors from the potential optimized donors, wherein the one or more recommended optimized donors are identified based at least in part on their past show rate and successful collection rate; and
generating, by the one or more processors, a list of the one or more recommended optimized donors.

5. The method of claim 4, further comprising:
identifying, by the one or more processors, contact information for at least one of the one or more recommended optimized donors, and contacting at least one of the one or more recommended optimized donors to recruit for a donation.

6. The method of claim 4, wherein a previous donor is identified as one of the one or more recommended optimized donors based, at least in part, on one or more of following characteristics of the previous donor: donor eligibility, platelet count, date of last donation, amount of component donated within a given time period, existence of the past unsuccessful donation attempts, gender, height, weight, or blood type.

7. The method of claim 4, further comprising:
comparing, by the one or more processors, the scheduled blood component with one or more blood components associated with current or anticipated demand.

8. The method of claim 4, wherein transmitting the modification comprises transmitting, by the one or more processors, to a blood collection device, a signal comprising instructions to collect the desired blood components.

9. The method of claim 4, wherein transmitting the modification comprises outputting, by the one or more processors, the modification on a day of collection on which input data identifying a present donor is received.

10. The method of claim 4, further comprising:
determining and recommending, by the one or more processors, a maximum safe collection amount.

11. The method of claim 10, further comprising:
comparing, by the one or more processors, the scheduled blood component with one or more blood components associated with current or anticipated demand.

12. The method of claim 10, further comprising:
transmitting, by the one or more processors, to a blood collection device, a signal comprising instructions to collect the desired blood components.

13. The method of claim 4, further comprising:
determining, by the one or more processors, that a donation potential is maximized by determining a maximum volume or number of products allowable based on a past donation history of a present donor.

14. The method of claim 4, further comprising:
transmitting, by the one or more processors, the modification on a day of collection on which input data identifying a present donor is received.

15. One or more non-transitory storage devices configured to store instructions thereon that, when executed by one or more processors, cause the one or more processors to:

receive biometric inputs at a workstation of a blood center to identify a donor;

access, based on the identifying, a scheduled appointment for the donor including an identification of a scheduled blood component to be collected from the donor;

access a user profile of the donor;

determine, from the user profile, an eligibility for the donor based on unsuccessful donation attempts of the donor in past;

determine based on a number of times the donor donated in the past, that the donor is eligible to donate again;

determine, in real-time, that a need for desired blood components desired by the blood center is greater than that for the scheduled blood component;

determine a device capability of a blood component collection machine in collecting the desired blood components during the scheduled appointment;

modify the scheduled appointment based on the determined eligibility, the determined need and the determined device capability;

transmit the modification for display at the workstation;

automatically begin collection of the desired blood components, using the blood component collection machine, upon selection of the desired blood components;

read, using the blood component collection machine, an RFID chip at a time of the collecting of the desired blood components;

add, based on the reading, the desired blood components to an electronic inventory log;

read, using the blood component collection machine, the RFID chip when the desired blood components are removed from storage in the blood center to automatically update a status of the desired blood components in the electronic inventory log;

determine, using the electronic inventory log, respective ones of the desired blood components that have been quarantined or recalled;

identify a location of the respective ones of the desired blood components when the respective ones of the desired blood components have been quarantined or recalled; and display an alert using the electronic inventory log, when the respective ones of the desired blood components are quarantined or recalled.

16. The one or more non-transitory storage devices of claim 15, wherein the instructions further cause the one or more processors to determine and recommend a maximum safe collection amount.

17. The one or more non-transitory storage devices of claim 16, wherein the instructions further cause the one or more processors to compare the scheduled blood component with one or more blood components associated with current or anticipated demand.

18. The one or more non-transitory storage devices of claim 16, wherein the instructions further cause the one or more processors to transmit, to a blood collection device, a signal comprising instructions to collect the desired blood components.

19. The one or more non-transitory storage devices of claim 16, wherein the instructions further cause the one or more processors to determine that a donation potential is maximized by determining a maximum volume or number of products allowable based on a past donation history of a present donor.

20. The one or more non-transitory storage devices of claim 16, wherein the instructions further cause the one or more processors to transmit the modification on a day of collection on which input data identifying a present donor is received.

* * * * *